Figure 1A:
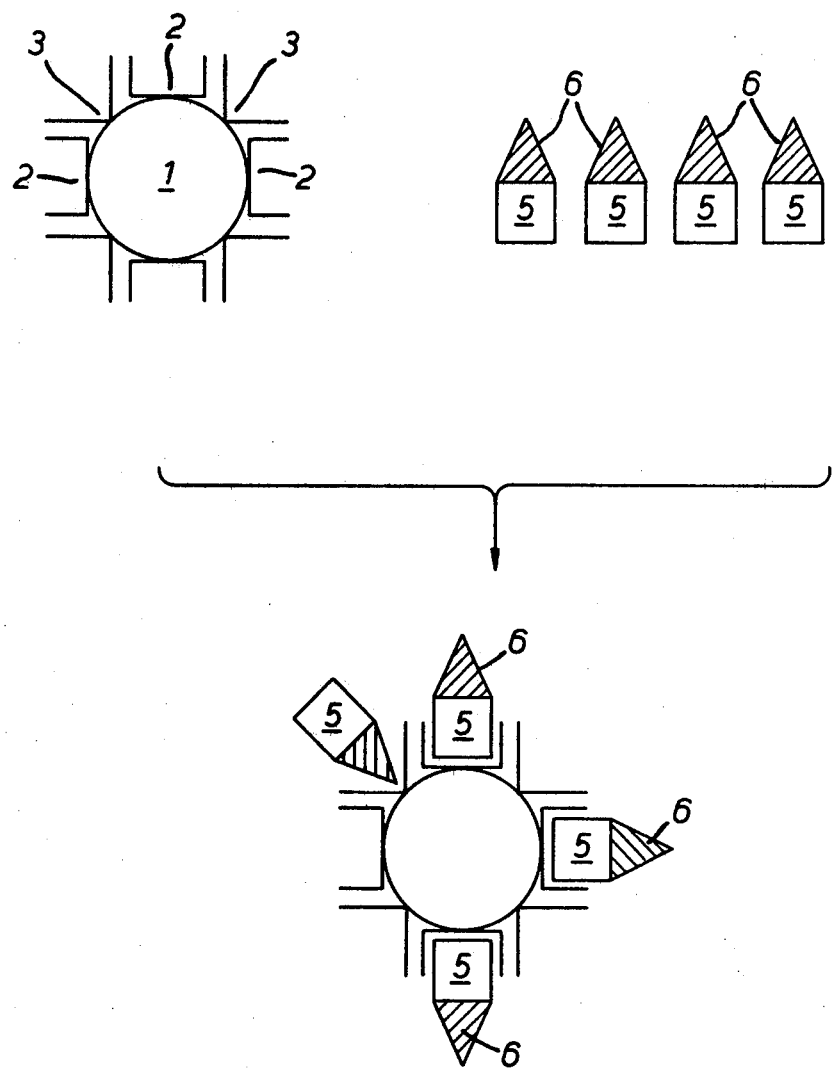

United States Patent [19]

Smith

[11] 4,401,764

[45] Aug. 30, 1983

[54] IMMUNOASSAYS EMPLOYING LABELED REAGENT AND A CONJUGATE HAVING TWO BINDING SITES

[75] Inventor: David S. Smith, London, England

[73] Assignee: Technicon Instruments Corporation, Tarrytown, N.Y.

[21] Appl. No.: 230,477

[22] Filed: Feb. 2, 1981

[30] Foreign Application Priority Data

Feb. 7, 1980 [GB] United Kingdom ............... 8004090

[51] Int. Cl.$^3$ ..................... G01N 33/48; G01N 33/52; G01N 33/54; G01N 33/78

[52] U.S. Cl. ..................................... 436/500; 424/7.1; 436/531; 436/532; 436/533; 436/534; 436/546; 436/547; 436/805; 436/815; 436/819; 436/828

[58] Field of Search ............................. 424/8, 12, 7.1; 23/230 B; 435/7; 436/500, 531, 532, 533, 534, 537, 546, 547, 805, 815, 819, 828

[56] References Cited

U.S. PATENT DOCUMENTS 3,996,345 12/1976 Ullman ................................. 424/12
4,108,976 8/1978 Reese ................................. 424/12 X
4,161,515 7/1979 Ullman ................................. 424/12

OTHER PUBLICATIONS

Nargessi et al., J. Immunol. Methods, vol. 26, 1979, pp. 307–313.

*Primary Examiner*—Anna P. Fagelson
*Attorney, Agent, or Firm*—S. P. Tedesco; C. J. Herron

[57] ABSTRACT

In the immunoassay of antigens in liquids, a reaction mixture is formed containing the liquid under assay, labelled antigen, and a mixed binding reagent which contains an antigen-binding site and a label-binding site, the two sites being spaced apart in the reagent so that a single molecule of labelled antigen cannot bind to both sites. The label is one whose activity is changed upon binding to a label-binding site, and the amount of antigen in the original liquid sample is determined by measuring the activity of the label in the reaction mixture. A preferred label is a fluorophore. The mixed binding reagent preferably consists of two antibodies linked together.

21 Claims, 6 Drawing Figures

IMMUNOASSAYS EMPLOYING LABELED REAGENT AND A CONJUGATE HAVING TWO BINDING SITES

This invention relates to the immunoassay of antigens (which term includes haptens), using a labelled reagent.

Immunoassays which utilize the immunospecific reaction between an antibody and an antigen are well known. It is also known to use in such assays a labelled reagent, part of which becomes bound and part remains free in the reaction mixture, and to determine quantitatively the antibody or antigen under assay by measuring the amount of free or bound labelled reagent. In certain assays of this type, such as radioimmunoassays, it is necessary to separate the bound labelled reagent from the free labelled reagent before measuring the amount of label, and this separation step is not only time-consuming but can be a source of error. Attention has therefore been focussed in recent years on providing an immunoassay in which a separation step is unnecessary, and several workable proposals have been made, including some utilising a fluorophore label.

In fluoroimmunoassays, the amount of bound or free fluorophore-labelled reagent is measured by fluorescence. In the fluoroimmunoassays of certain antigens, the fluorescence of the labelled reagent changes when it becomes bound, so that a separation step is then unnecessary. Such an assay is described in our U.S. Pat. No. 4,150,949 and may be used to assay haptens such as gentamicin. This change in fluorescence does not occur with all antigens, however, and in an alternative approach, the fluorescence of the free fluorophore-labelled reagent in the assay mixture is quenched by introducing the antibody to the fluorophore-label. Thus the antigen to be assayed is mixed with fluorophore-labelled reagent and with antibody to the antigen, and part of the reagent becomes bound and part remains free in the mixture. Antibody to the fluorophore is then added, which binds to the free reagent and changes (usually quenches) the fluorescence thereof. The net resulting fluorescence of the mixture gives a measure of the amount of labelled reagent originally bound to the antibody against the antigen.

While this procedure is satisfactory with certain antigens, the problem arises that in some cases, the antibody to the label will bind not only with the free labelled reagent but also with the bound labelled reagent. We have now devised a way of overcoming this problem.

In one aspect, the present invention provides a method of immunoassay of an antigen (Ag) in a liquid sample, which comprises forming a mixture of:
 (a) sample;
 (b) a substance bearing a non-radiosotopic label, which substance is the same as the Ag under assay or is so closely similar as to be bindable by an antibody against the Ag;
 (c) an antibody against the Ag;
and detecting the amount of label activity in the mixture and therefrom determining the amount of Ag; characterised in that: component (c) is a mixed binding reagent which comprises at least one first site selectively bindable to the Ag, and at least one second site selectively bindable to the label, the first and second sites being spaced apart so that a single molecule of labelled substance cannot simultaneously become bound to both a first and a second site, and wherein the activity of the label is changed upon binding to the second sites.

The method of the invention is applicable to assays utilising labels such as fluorophores (or potential fluorophores), spin labels, chemiluminescent labels and, in certain circumstances, enzyme or coenzyme labels. Preferably, however, a fluorophore (or potential fluorophore) label is used and the invention will hereafter be described principally with reference to fluoroimmunoassays, it being understood that in principle and mutatis mutandis other labels such as described may be used. By "potential fluorophore label", we mean a label which does not normally fluorescence but which can be made to fluoresce.

An important feature of the invention is the mixed binding reagent (hereinafter MBR) utilised in step (c). This reagent will normally comprise two antibodies (one against the antigen under assay and the other against the label), the two different antibodies being linked together to form a unitary reagent complex in which the first and second binding sites are spaced apart so that each molecule of the labelled substance can only bind to one site and not simultaneously to both. Thus, in the assay of the invention, the problem encountered in the prior art of a molecule of the labelled substance becoming bound to both types of antibody, is overcome.

The assay of the invention proceeds generally as follows. The sample containing the antigen under assay is mixed with the labelled substance and the MBR. The antigen and the labelled substance compete for the first (i.e. antigen-binding) sites in the MBR. The fluorescence of the labelled reagent is preferably such that it does not change significantly when the substance binds to a first site in the MBR.

The portion of labelled reagent which does not bind to a first site in the MBR is available to bind, via its label, to a second (i.e. label-binding) site in the MBR whereupon its fluorescence will change markedly. Overall, the net resulting fluorescence of the mixture will vary with the amount of Ag present in the original sample, since this affects the amount of labelled reagent both remaining free and becoming bound to second sites in the MBR. By first preparing standard results relating fluorescence to antigen concentration, the amount of antigen in any sample can be determined.

The MBR is an important feature of the present invention. It comprises two different types of binding site which are spaced apart so as to prevent a molecule of the bifunctional labelled substance becoming bound to both types of site. The binding sites themselves are most preferably provided by antibodies or by fragments of antibodies containing their binding sites, although one or both sites may be provided in the form of active chemical groups other than an antibody. A convenient and preferred MBR comprises an antibody to the antigen (to provide first sites), and an antibody to the label (to provide second sites), the two antibodies being linked together in a manner such as to achieve the desired spacing. In one convenient type of MBR, the two antibodies providing the binding sites are linked by a "second" antibody. Thus, the two binding site-antibodies are raised in the same animal species (e.g. rabbit) and are then linked by an antibody (the "second" antibody) to the immunoglobulin of that species (e.g. by sheep (anti-rabbit Ig) antibodies). In this way, the two rabbit-generated antibodies are so located that their respective binding sites for the antigen and label are spaced so that a molecule of labelled substance cannot simultaneously bind to both sites.

The second antibody is only one of the various ways in which the antigen-binding and label-binding antibodies (or other binding substances) can be linked to form an MBR Another possibility is to use protein A in place of the second antibody. Alternatively, both the antigen-binding and the label-binding antibodies can be conjugated with a hapten (or, more generally, an antigen), and then bound by the addition of an antibody to the hapten. Using this technique, it is not necessary for the antigen-binding and label-binding antibodies to have been raised in the same animal species.

Another possibility is for the two antibodies to be linked to a solid substrate. A particularly preferred such substrate is polyacrylamide beads which are known for use in fluoroimmunoassays, and which have a specific gravity close to 1 and also a refractive index close to that of water so that they do not seriously interfere with the fluorescence measurement by light scattering. Such beads are commercially available. By activating the surfaces of the beads, the two antibodies can be covalently or otherwise bound thereto to provide an MBR for use in the present invention.

Another way of preparing an MBR is to link the two antibodies together using a bifunctional chemical bridging group of an appropriate kind, many of which are well known in protein chemistry.

The preferred fluorophore labels are fluorescein, dansyl, rhodamine, fluorescamine, pyrene, 2-methoxy-2,4-diphenyl-3(2H)-furanone, and umbelliferone and derivatives thereof. Of these, fluorescein is the most preferred. The label must be one whose activity (e.g. fluorescence) is changed upon binding to a second site.

The method of the present invention is widely applicable to the assay of antigens, but it is particularly of interest in the assay of haptens, such as gentamicin and similar aminoglycoside antibiotics, and phenytoin and nortriptyline and similar drugs. It can also be used for the assay of thyroid hormones such as thyroxine ($T_4$), although normally in the assay of human sera for $T_4$ or nortriptyline, there will be significant fluorescence interference unless the serum is first treated to remove the interferants.

The nature of the labelled substance is not critical except that it must be bindable by the antibody against the antigen under assay, and also the fluorescence (or other activity) of the label must change when the label binds to the anti-label binding sites in, for example, an antibody. Generally, the substance will be the same as the antigen under assay, but where it is difficult to bind a label to the antigen, then another substance is used which is sufficiently similar to the antigen to bind to the antigen binding sites in the MBR.

The method of the invention may be carried out on a discrete manual basis, or in an automated fashion on a plurality of samples using, for example, the well known continuous flow techniques. In continuous flow analyses according to the present invention, the mixture of sample, fluorescent labelled substance and MBR, is passed along a conduit and the fluorescence is then measured. In a preferred procedure, which is described in U.S. Pat. No. 2,797,149, individual segments of mixture are passed sequentially along the conduit, separated by an inert fluid segment (e.g. air) and, if desired, a wash liquid segment. The mixture can be formed in the conduit itself, by supplying to the conduit, in phase with segments of components of the mixture already present therein, the one or more further components, mixing of the components occurring in the conduit as the mixture flows therethrough.

The following experimental results illustrate the method of the invention.

1. ASSAY OF THYROXINE ($T_4$)

Materials

L-$T_4$, as the free acid, was obtained from Sigma and labelled with fluorescein isothiocyanate as described in our copending U.K. application No. 38710/76 Rabbit anti-fluorescein serum and sheep anti-rabbit immunoglobulin G serum were prepared by standard methods. Rabbit and sheep anti-$T_4$ sera were obtained from Dr. G. Zborowski (Technicon Instruments Corp., Tarrytown, N.Y., U.S.A.) and Dr. T. G. Merrett (Benenden Chest Hospital, Cranbrook, Kent, U.K.), respectively.

All experiments were performed using 75 mmol/l barbital buffer, pH 8.6 at ambient temperature.

Methods

Fluorimetry

Fluorescence was measured using a Perkin-Elmer Model 1000 fluorimeter, fitted with appropriate filters. In the experiments a correction was made for the background signal contributed by reactants other than fluorescein-labelled $T_4$. This was determined by fluorimetry of incubation mixtures containing no labelled hormone. Results were expressed relative to an arbitrary scale of fluorescence intensity.

Fluorescence of labelled $T_4$ in presence of antibody excess

To 500 $\mu$l of fluorescein-labelled $T_4$ (30 $\mu$g/l) was added 500 $\mu$l of antiserum, control serum or buffer, followed after at least 5 min by the addition of 500 $\mu$l of a different antiserum, control serum or buffer. Fluorescence was determined as above. Rabbit anti-fluorescein and rabbit control serum were present at a final dilution of 1:6400 and sheep anti-$T_4$ serum and sheep control serum at a final dilution of 1:400.

Fluorescence of labelled $T_4$ in the presence of doubling antiserum dilutions

To 500 $\mu$l aliquots of doubling dilutions of rabbit anti-$T_4$, sheep anti-$T_4$, rabbit anti-fluorescein and control sera from sheep and rabbits was added 1 ml of fluorescein-labelled $T_4$ (15 $\mu$g/l). Fluorescence was determined after an incubation period of at least 5 min.

Formation of mixed binding reagent

To 500 $\mu$l aliquots of doubling dilutions of sheep anti-rabbit immunoglobulin G serum was added 500 $\mu$l of a mixture of rabbit anti-$T_4$ and rabbit anti-fluorescein serum. After 60 min, 500 $\mu$l of fluorescein-labelled $T_4$ (30 $\mu$g/l) was added and the fluorescein measured as above.

Fluoroimmunoassay of the invention using a mixed binding reagent

The mixed binding reagent was first prepared as above. To 100 $\mu$l of aliquots of standard solutions of $T_4$ in buffer was added 650 $\mu$l of fluorescein-labelled $T_4$ (23 $\mu$g/l) followed by 750 $\mu$l of the mixed antibody complex and the fluorescence was then determined as above. A control experiment was performed in an identical manner except that a sheep control serum was used in place of the sheep anti-rabbit immunglobulin G serum.

RESULTS

Fluorescence of labelled $T_4$ in the presence of antibody excess

The results are summarised in Table 1. Addition of sheep anti-$T_4$ serum in place of buffer resulted in the expected enhancement of fluorescence (from 16 to 42 fluorescence units) which was not affected significantly by the presence of rabbit control serum. Conversely, addition of rabbit anti-fluorescein serum in place of buffer caused a marked decrease in fluorescence (from 16 to 2 fluorescence units) unaffected by sheep control serum. Irrespective of the order of addition, the fluorescence of fluorescein-labelled $T_4$ was largely quenched in the presence of both the anti-$T_4$ and anti-fluorescein sera, relative to the signal when bound by antibodies to $T_4$ alone. In all cases the reaction was complete within 1 min as judged by attainment of stable fluorescent read-out.

Fluorescence of labelled $T_4$ in the presence of doubling antiserum dilutions

Figure 2:
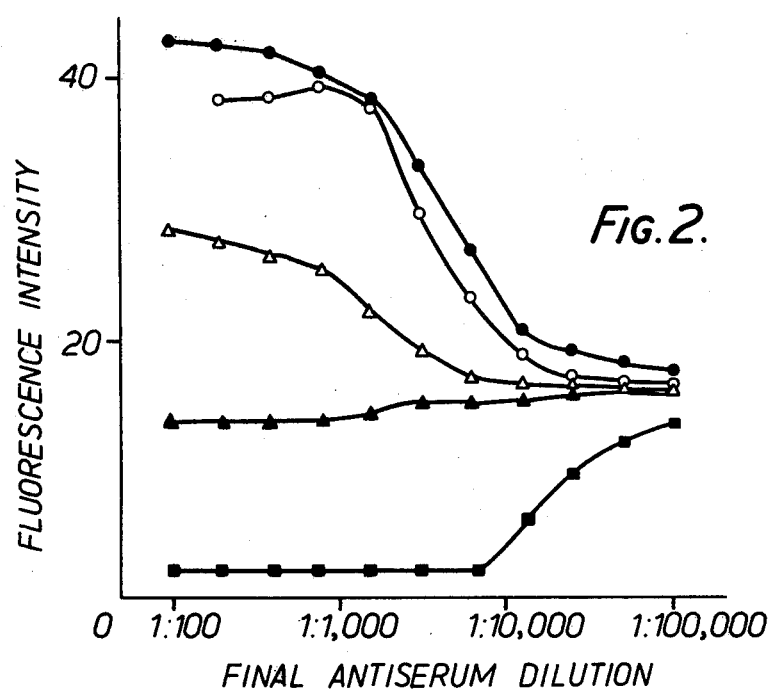

Rabbit anti-$T_4$ and rabbit anti-fluorescein dilution curves were obtained in order to choose appropriate dilutions of these antisera for use in forming the mixed binding reagent. A sheep anti-$T_4$ dilution curve was also obtained and the results are shown in FIG. 2, together with the results using control rabbit and sheep sera. Binding of fluorescein-labelled $T_4$ by antibodies to $T_4$ and to fluorescein resulted in the expected enhancement and quenching of fluorescence, respectively. Non-specific effects were negligible. On the basis of these studies a final dilution of rabbit anti-$T_4$ of 1:1600 and of rabbit anti-fluorescein of 1:6400 was chosen to form the mixed anti-body reagent.

Formation of mixed binding reagent

Figure 3:
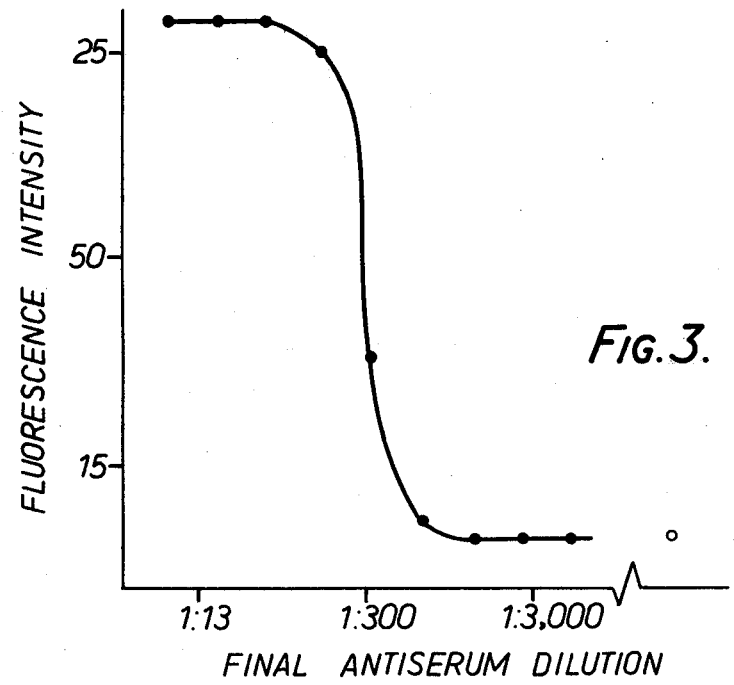

The fluorescence of fluorescein-labelled $T_4$ added to a mixture of rabbit anti-$T_4$ and anti-fluorescein sera was increased some two-fold by prior complexation of the antibodies with sufficient amounts of sheep anti-rabbit immunoglobulin G serum (FIG. 3). On the basis of this experiment a final dilution of sheep antiserum of 1:160 was chosen to form the mixed binding reagent. Prior incubation of the two rabbit antisera with serum from a control sheep had no significant effect.

Fluoroimmunoassay of the invention using mixed binding reagent

Using the mixed binding reagent, a standard curve for $T_4$ was obtained (FIG. 4) with the addition of increasing amounts of unlabelled $T_4$ causing a progressive decrease in the final fluorescence reading The control experiment confirmed the dependence of the observed effects on the presence of specific sheep anti-rabbit immunoglobulin G serum.

The background signal from reagents other than the labelled $T_4$ was 10 units and was largely contributed by the intrinsic fluorescence of the relatively high concentration of sheep antiserum present. The standard curve obtained employing a mixed binding reagent 24h after preparation was the same as that obtained after 60 min although the mixed binding reagent had developed visible turbidity and the background signal had increased to 12 fluorescence units.

TABLE 1

| Fluorescence of Fluorescein-labelled $T_4$ in the Presence of Antibody Excess | | |
|---|---|---|
| Order of Reagent Addition to Labelled $T_4$ | | Fluorescence |
| First Reagent | Second Reagent | Intensity |
| Buffer | Buffer | 16 |
| Anti-$T_4$ serum* | Buffer | 42 |
| Anti-$T_4$ serum | Rabbit control serum | 41 |
| Anti-fluorescein serum | Buffer | 2 |
| Anti-fluorescein serum | Sheep control serum | 2 |
| Anti-fluorescein serum | Anti-$T_4$ serum | 6 |
| Anti-$T_4$ serum | Anti-fluorescein serum | 10 |

*The antiserum dilutions employed are given in the methods section

2. ASSAY OF AMIKACIN

Materials

The following reagents were used: rabbit anti-fluorescein serum; rabbit anti-amikacin serum; sheep anti-rabbit immunoglobulin G serum; and fluorescein-labelled amikacin prepared by the reaction of amikacin with fluorescin isothiocyanate. The buffer used was 100 mmol/l sodium phosphate, pH 7.5, containing 1 ml/l Triton X-100 detergent and 1 g/l sodium azide.

Formation of mixed binding reagent

To a mixture of anti-fluorescein serum and anti-amikacin serum was added anti-rabbit immunoglobulin G serum, so as to give final dilutions of the antisera as follows: anti-amikacin 1:320; anti-fluorescein 1:2,000; and anti-rabbit immunoglobulin G 1:40. The mixture was left at room temperature for 1 hour before use.

Assay procedure

Figure 5:
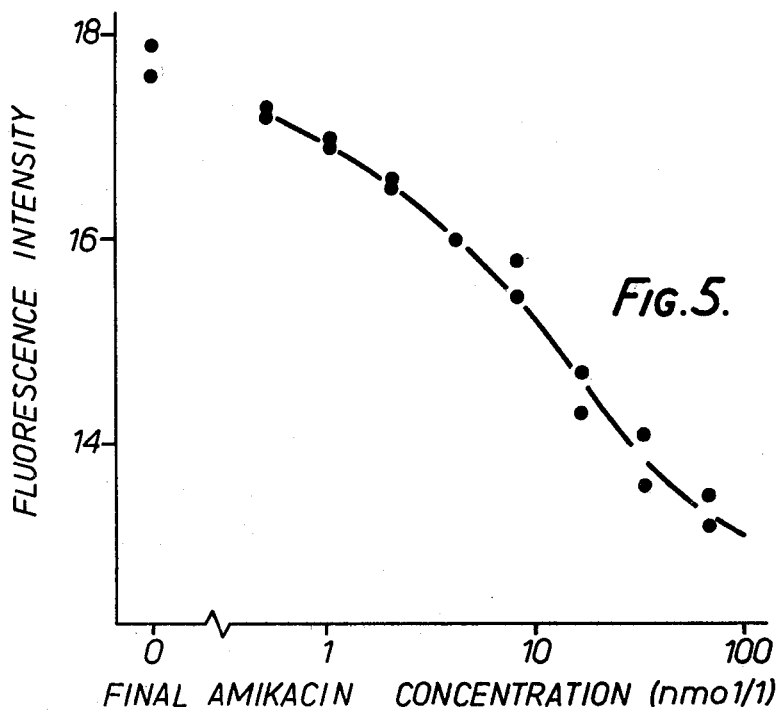

To 50 $\mu$l aliquots of standard solutions of amikacin in buffer was added 750 $\mu$l of fluorescein-labelled amikacin (20 nmol/l concentration estimated spectrophotometrically), followed by 750 $\mu$l of mixed binding reagent. After incubation for 30 min at room temperature, the fluorescence of the mixtures was determined. Correction was made for the background signal contributed by reactants other than fluorescein-labelled amikacin; this was determined by measurement of the fluorescence of mixtures containing no labelled antibiotic. Results were expressed relative to an arbitrary scale of fluorescence intensity. The standard curve obtained is shown in FIG. 5.

Figure 1B:
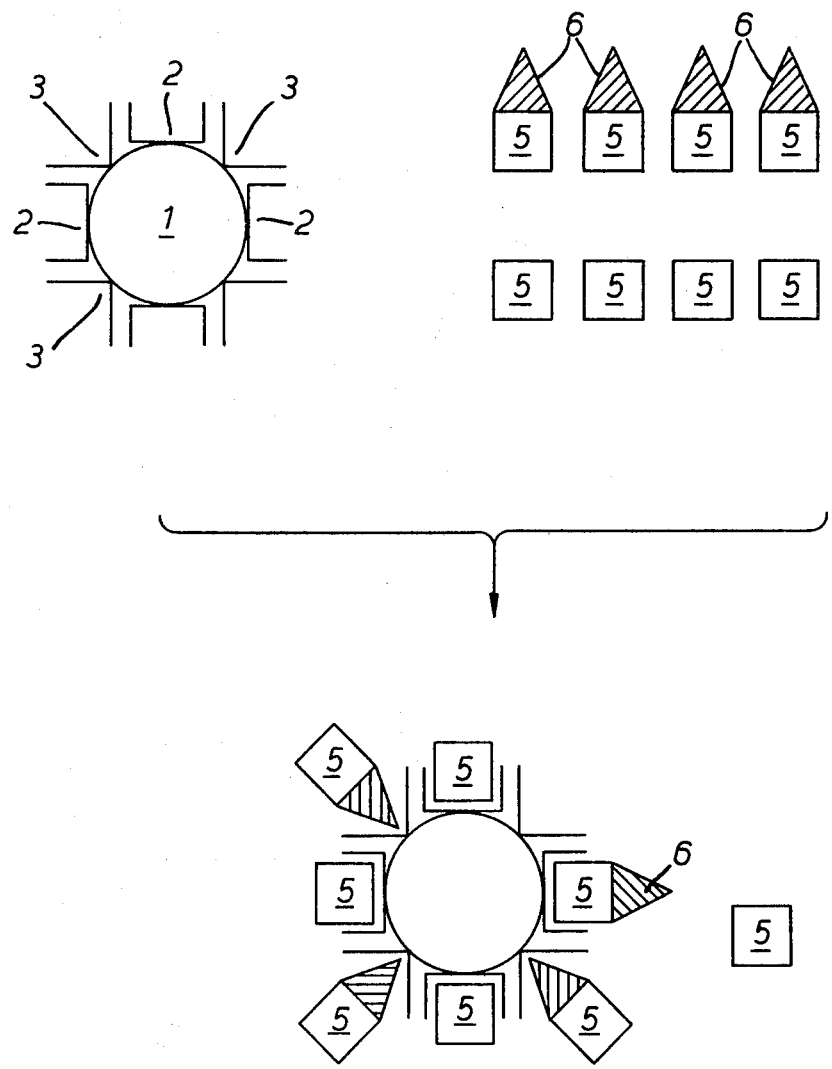

In the accompanying drawings:

FIGS. 1A and 1B are a diagrammatic representation of one embodiment of the method of the invention as applied to fluoroimmunoassays. In FIGS. 1A and 1B, the mixed binding reagent 1 has anti-hapten binding sites 2 and anti-label binding sites 3. In FIG. 1A, the hapten 5 carries a fluorescein label 6. In FIG. 1B, some of the hapten 5 is labelled and some is not. In FIG. 1A, when the labelled hapten is incubated with the MBR 1, some of the labelled hapten will be bound to the anti-hapten sites 2 and continue to fluoresce, while some will be bound by the anti-fluorescein sites 3 with a resultant decrease in fluorescence. In FIG. 1B unlabelled hapten is also present in the reaction mixture. This competes with labelled hapten for anti-hapten binding sites 2, and as more labelled hapten becomes bound to anti-fluorescein sites 3, there will be a further decrease in fluorescence. Thus the fluorescence of the incubation mixtures at equilibrium will be inversely related to the initial amount of unlabelled hapten present.

FIG. 2 shows anti-$T_4$ and anti-fluorescein dilution curves. Closed circles, sheep anti-$T_4$ serum; open circles, rabbit anti-$T_4$ serum; closed triangles, control sheep serum; open triangles, control rabbit serum; closed squares, anti-fluorescein serum.

FIG. 3 is an anti-immunoglobulin G dilution curve in formation of mixed antibody reagent. Final dilutions: anti-T₄ serum 1:1600; anti-fluorescein serum 1:6400. Open circle shows fluorescence in absence of added anti-immunoglobulin G serum.

Figure 4:
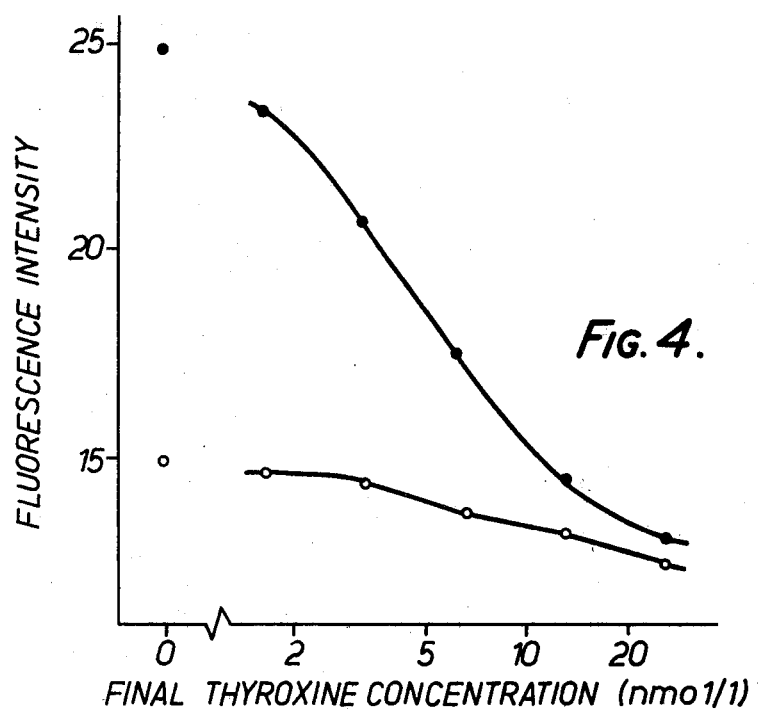

FIG. 4 is the fluoroimmunoassay standard curve. Closed circles, using mixed binding reagent; open circles, anti-immunoglobulin G serum replaced by control sheep serum. Final dilutions: anti-T₄ serum 1:1600; anti-fluorescein serum 1:6400; anti-immunoglobulin G serum or control sheep serum 1:160.

FIG. 5 is the fluoroimmunoassay standard curve for the assay of amikacin.

I claim:

1. A method of immunoassay of an antigen in a liquid sample, which comprises forming a mixture of:
   (a) sample;
   (b) a substance bearing a non-radioisotopic label, which substance is the same as the antigen under assay or is so closely similar as to be bindable by an antibody against the antigen; and
   (c) a mixed binding conjugate which comprises at least one first site selectively bindable to the antigen, and at least one second site selectively bindable to the label, the first and second sites being spaced apart so that a single molecule of labelled substance cannot simultaneously become bound to both a first and a second site, and wherein the activity of the label is changed upon binding to the second site; and detecting the amount of label activity in the mixture and therefrom determining the amount of antigen.

2. The method of claim 1 wherein the label is a fluorophore or a potential fluorophore, and the activity is fluorescence.

3. The method of claim 1 wherein component (c) comprises an antibody against the antigen and an antibody against the label, the two antibodies being linked together to form a unitary mixed binding reagent complex.

4. The method of claim 3 wherein the two antibodies have been raised in the same animal species and are linked together by an antibody to the immunoglobulin of that species.

5. The method of claim 4 wherein the two antibodies have been raised in rabbits and the linking antibody has been raised in sheep.

6. The method of claim 3 wherein the two antibodies are linked together by protein A.

7. The method of claim 3 wherein the two antibodies are linked to a solid substrate.

8. The method of claim 7 wherein the solid substrate is finely divided solid particles, each particle bearing both antibodies.

9. The method of claim 8 wherein the solid particles are polyacrylamide beads.

10. The method of claim 3 wherein the two antibodies are linked together by a bifunctional chemical bridging group.

11. The method of claim 3 wherein each antibody is conjugated with a hapten, and the bound haptens are cross-linked to form unitary mixed binding reagent complexes containing both antibodies.

12. The method of claim 11 wherein the haptens are cross-linked by antibodies against the hapten.

13. The method of claim 1 which is carried out on a discrete manual basis.

14. The method of claim 1 which is carried out on an automated continuous flow basis.

15. The method of claim 1 wherein the antigen under assay is gentamicin or another aminoglycoside antibiotic, phenytoin, nortriptyline, or a thyroid hormone.

16. A specific binding assay method for determining an analyte in a liquid, which method comprises
   combining said liquid with a non-radioisotopically labeled analyte or analyte analog and a conjugate comprising an analyte binding partner linked with a label binding partner, said binding partners being spaced apart so that a labeled analyte or analyte analog cannot simultaneously bind with the analyte binding partner and the label binding partner; and measuring any resultant change in label signal.

17. The method of claim 16 wherein the analyte binding partner is linked with the label binding partner through at least one protein A molecule.

18. The method of claim 16 wherein the analyte binding partner and the label binding partner are antibodies and are linked by an antibody to said binding partner antibodies.

19. The method of claim 16 wherein the analyte binding partner and the label binding partner are each conjugated with an antigen and the antigen of each of said conjugates is bound to a common antibody therefor.

20. The method of claim 16 wherein the analyte binding partner and the label binding partner are linked to a solid substrate.

21. The method of claim 20 wherein the solid substrate is comprised of polyacrylamide beads having a specific gravity of about one and a refractive index which is close to that of water.

* * * * *